(12) United States Patent
Blasenheim

(10) Patent No.: US 6,510,007 B1
(45) Date of Patent: Jan. 21, 2003

(54) FLOW CYTOMETRY LENS SYSTEM

(75) Inventor: Barry J. Blasenheim, San Jose, CA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/934,741

(22) Filed: Aug. 21, 2001

(51) Int. Cl.[7] ................................................ G02B 21/02
(52) U.S. Cl. ...................................... 359/659; 359/656
(58) Field of Search ............................... 359/656, 659, 359/756

(56) References Cited

U.S. PATENT DOCUMENTS

| | | | | |
|---|---|---|---|---|
| 3,138,651 A | * | 6/1964 | Ruben ......................... | 359/656 |
| 5,798,869 A | * | 8/1998 | Watanabe .................... | 359/658 |
| 5,805,346 A | | 9/1998 | Tomimatsu .................. | 359/656 |
| 5,978,147 A | * | 11/1999 | Kudo .......................... | 359/656 |
| 5,982,559 A | * | 11/1999 | Furutake ..................... | 359/656 |

* cited by examiner

*Primary Examiner*—Georgia Epps
*Assistant Examiner*—David N. Spector
(74) *Attorney, Agent, or Firm*—Thomas Schneck; David M. Schneck

(57) ABSTRACT

A flow cytometry lens system features a low (<1.55) refractive index, near hemispheric plano-convex lens nearest a cytometry flow cell with the planar surface on the object side of the system and a convex surface with a radius of curvature in a range from 3.5 to 5.5 mm, followed by a pair of positive meniscus lenses having the concave sides facing the object side, with the surfaces of the second meniscus lens less sharply curved than the corresponding surfaces of the first meniscus lens, which in turn is followed by a positive doublet lens. The lens elements are optimized for providing a working distance of at least 1.75 mm, a field of view of at least 400 µm, a numerical aperture of at least 1.19 and a lens magnification in excess of 10.

6 Claims, 1 Drawing Sheet

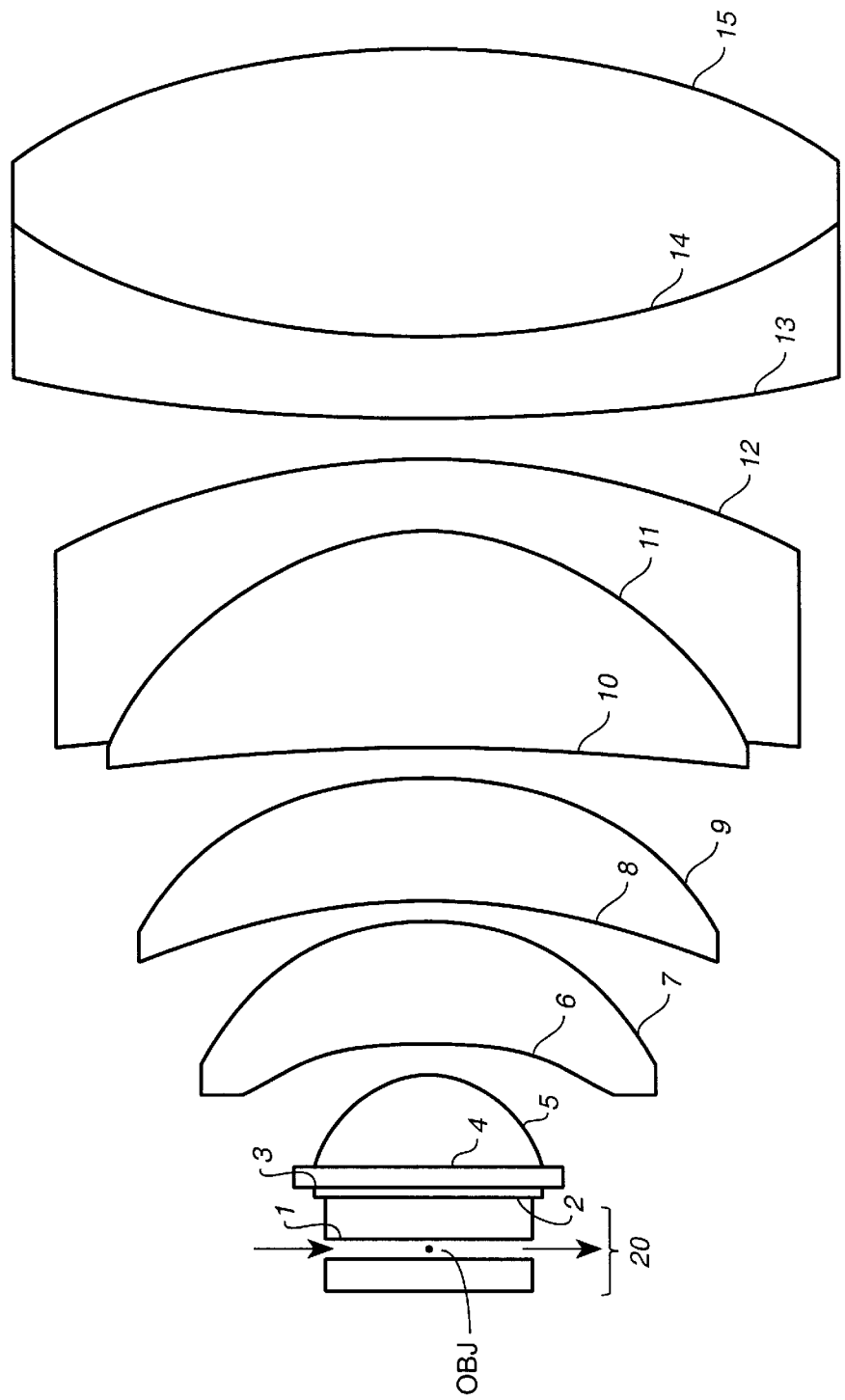
FIG._1

FLOW CYTOMETRY LENS SYSTEM

TECHNICAL FIELD

The present invention relates to optical systems, and in particular lenses. The invention also relates to flow cytometry, and in particular microscope lens systems adapted for magnifying and imaging the target objects (cells, cellular clusters, particles, etc.) in a flow cell and for collecting light scattered therefrom.

BACKGROUND ART

In a cytometer, objects, such as flourescent-labeled cells or particles, flow through a cuvette or other flow cell in water or saline solution. A light source illuminates a volume of the flow cell. This illumination system may include an optical fiber and condenser lens. The gap between the illumination system and the cuvette may be filled with an immersion oil to give the illumination system a high numerical aperture (about 1.2) needed to completely fill the numerical aperture of a microscope lens system located on the opposite side of the cuvette. This microscope lens system is specially adapted to magnify and image the objects within the cuvette. There may be a number of translation stages provided for making fine positioning adjustments to the system, but otherwise the various components remain stationary relative to one another, except of course for the cell or particle containing liquid flowing within the cuvette. Alternatively, the lens may be used to collect light scattered from the flow cell, as well as fluorescent light.

Fluid-immersed microscope lens systems are known. Two examples of such lenses are disclosed in U.S. Pat. No. 5,805,346 to Tomimatsu. Its first embodiment begins with a negative meniscus, flint glass (high refractive index of about 1.77) lens with the sharply curved concave surface of that lens in contact with the immersion fluid. This is followed by a positive meniscus lens, a plano-convex lens, a doublet lens with overall biconvex profile, a triplet lens with overall biconvex profile, and doublet lens with overall meniscus profile and having the convex surface facing the object side. That patent's second embodiment also begins with a negative meniscus, flint glass lens with its sharply curved concave surface again in contact with immersion fluid. This is followed by a single positive meniscus lens, a pair of positive doublets, the first having a slightly meniscus overall shape, and finally a plano-concave doublet. Tomimatsu states that by making the first lens surface concave, the refractive index of the first lens can be higher than the immersion fluid and can have a negative refractive power. This in turn is disclosed to permit better correction of Petzval curvature. While the exact lens materials used are not named, the disclosed index and dispersion values suggest the use of relatively expensive material types, including possibly lanthanum flints and fluor and phosphate crowns.

A prior lens of Becton Dickinson, the assignee of the present invention, has a plano-convex flint glass lens followed by a single meniscus lens, and a pair of doublets, the first having a plano-convex overall shape and the second being biconvex. That lens has a fluid-immersed numerical aperture of 1.17, and a resolution that is characterized by a geometric spot size in the image field for point objects of 442.6 µm (full field) and 365.2 µm (on-axis) and by a circle radius (80% energy containment) of about 500 µm. Its working distance is about 2 mm.

Improvements are sought for flow cytometry lenses in both resolution and working distance while still maintaining, or preferably also improving, numerical aperture and field of view. In particular, a resolution in which image spot sizes are less than 100 µm (both on-axis and full field) and a circle radius (at 80% energy containment) of less than 200 µm diameter is desired. Working distance should be at least 1.75 mm, the field of view should reach or exceed 400 µm diameter. Numerical aperture should at least match and preferably better 1.17.

DISCLOSURE OF THE INVENTION

These goals are achieved by a flow cytometry lens system that features a low index (less than 1.55, i.e. a crown glass) near-hemispheric positive plano-convex lens nearest the cytometry flow cell, with the planar surface on the object side, and a convex surface radius of curvature in the range of 3.5 to 5.5 mm. A pair of meniscus lenses follow this plano-convex lens, both meniscus lenses having their concave surfaces on the object side of the system. The second meniscus lens has surfaces that are less sharply curved than the corresponding surfaces of the first meniscus lens. The convex surface of the first meniscus lens is, in turn, less sharply curved than that of the plano-convex lens. The pair of meniscus lenses are followed by a pair of positive doublet lenses, the first having a slightly meniscus overall profile and the second having a biconvex overall profile.

The use of a crown glass for the first lens, plus the use of two meniscus lenses, improves the resolution of the system by reducing the amount of light bending at each refractive surface and thus significantly lowering aberrations without sacrificing numerical aperture or field of view at the desired magnification. Indeed, it is found that the field of view is more than doubled with this near-hemispheric plano-convex lens in the system. Also, the particular radius of curvature of its convex surface contributes to a longer working distance that meets the desired target distance.

BRIEF DESCRIPTION OF THE DRAWING

The FIGURE is a schematic side plan view of a preferred lens system embodiment in accord with the present invention.

BEST MODE FOR CARRYING OUT THE INVENTION

With reference to the Figure, a preferred embodiment of a lens system of the present invention is described according to the lens data contained in the following table. The numbered optical surfaces in the figure correspond to surface numbers in the leftmost column of the table. All radii and thickness values are in millimeters. Surface curvature tolerances for the lens data include 5 fringes for power (deviation of actual curvature from nominal curvature) and 1 fringe for irregularity (deviation from a perfect spherical surface). Tilt tolerance is 0.05 degrees from normal in any direction. Material tolerances are 0.0005 for refractive index and 0.8% for Abbe number.

| Surface | Radius of Curvature | Thickness | Thickness Tolerance | Aperture Radius | Clear Aperture Radius | Material |
|---|---|---|---|---|---|---|
| OBJ | 4 | 0.0889 | — | 0.2 | | Water |
| 1 | 4 | 1.94 | — | 4.6 | | Silica |
| 2 | 4 | 0.1682 | — | 4.6 | | Gel |

-continued

| Surface | Radius of Curvature | Thickness | Thickness Tolerance | Aperture Radius | Clear Aperture Radius | Material |
|---|---|---|---|---|---|---|
| 3 | 4 | 0.8 | .025 | 5.1 | 4.6 | BK7 |
| 4 | 4 | 3.915 | .025 | 4.6 | 4.6 | BK7 |
| 5 (AST) | −4.66 | 1.5 | .025 | 4.6A | 4.6 | Air |
| 6 | −16.918 | 5 | .05 | 8.5 | 7.3 | BK7 |
| 7 | −10.894 | 1 | .025 | 10 | 8.8 | Air |
| 8 | −26.836 | 5 | .10 | 11.5 | 10.2 | BK7 |
| 9 | −15.008 | 1 | .025 | 12.5 | 11.1 | Air |
| 10 | −103.704 | 9 | .10 | 13 | 11.9 | BK7 |
| 11 | −14.012 | 3 | .10 | 13 | 12.2 | SF8 |
| 12 | −34.38 | 2 | .05 | 15.5 | 14.1 | Air |
| 13 | +123.446 | 3 | .10 | 17 | 14.9 | SF8 |
| 14 | +34.38 | 12 | .10 | 17 | 15.1 | BK7 |
| 15 | −36.554 | 126.731 | .50 | 17 | 15.5 | Air |

The lens proper (surfaces 3 through 15) in this system is adapted to magnify and view cellular material within a cytometry flow cell or cuvette 20 (the flow cell inner and outer wall surfaces being optical surfaces 1 and 2 above). As indicated in the table, a flow cell has 0.007 inch (0.1778 mm) interior dimensions (wall-to-wall) and the cellular objects OBJ to be detected and analyzed are immersed in saline water flowing through the cell 20, nominally for lens design purposes through the center of the cell a distance of 0.0889 mm from the cell's inner wall. The 1.94 mm thick, fused silica, planar cell wall has a refractive index $n_d$ of 1.45857 and an Abbe number $v_d$ of 67.7. An optical gel layer provides an interface between the cytometry flow cell and the lens proper and improves lens mounting tolerances. The gel material is preferably NyoGel OC-431A sold by William F. Nye, Inc. of New Bedford, Mass., and has refractive indices at the 0.40 μm, 0.55 μm and 0.70 μm principal lens design wavelengths, respectively, of 1.487, 1.467, and 1.459. The gel should have a thickness less than 0.5 mm, and is selected in the above design to be 0.1682 mm thick. Other cytometry flow cells with different interior and wall dimensions, and other optical gels or oils could be used, with appropriate modifications in the lens specifications, optimized using commercially available software. Although lens positioning tolerances would be much tighter (0.025 mm or less), the lens could also be integrated with or mounted to the flow cell without using optical gel.

The lens glass types BK7 and SF8 (Schott glass designations) have been selected because they are relatively inexpensive stock materials that are easy to obtain in quantity, and because they are easy to grind and polish and don't stain easily. Other glass types could be used instead, including similar glass types from other optical glass suppliers, with appropriate modifications in the lens specifications. The optical glass designated BK7 [517642] has a refractive index $n_d$ of 1.51680 and an Abbe number $v_d$ of 64.17, and the optical glass designated SF8 [689312] has a refractive index $n_d$ of 1.68893 and an Abbe number $v_d$ of 31.18. All of the lenses in the preferred embodiment have spherical surfaces because they are inexpensive, more readily available in bulk, are more alignment tolerant, and are easier to assemble and test than aspheric lenses. However, if desired, modified lens specifications using one or more aspheric lenses have lower on-axis aberrations and could be used, although from a commercial standpoint the performance improvement likely would not be sufficient to justify their significantly greater expense and assembly difficulty.

The basic lens requirements include a numerical aperture of at least 1.17. (An object N.A. of 1.20±0.01 was used in obtaining the preferred embodiment that is set forth in the table above. A numerical aperture of 1.20 provides about 10 to 15% greater light collection than one of 1.17) The field of view should be at least 200 μm diameter and, if possible, as much as 400 μm or better. The present preferred embodiment has a field of view of 400 μm diameter. The working distance should be at least 1.75 mm, (2.2 mm is achieved in the preferred embodiment.) Most importantly, a lens system of less optical aberrations and high image quality is required for better resolution compared to existing cytometry lenses. In particular, the RMS spot size (a measure of resolution) in image space (for hypothetical point objects) for all wavelengths and all field points should be at most 100 μm. The present preferred embodiment achieves a calculated geometrical spot size of 85.04 μm at full field and of 71.86 μm on-axis. This puts a minimum of 80% of the optical energy of the image of an infinitely small point source within a circle of less than 200 μm diameter. This is a significant improvement over one existing cytometry lens design's 442.6 μm full field and 365.2 μm on-axis spot sizes and 800 μm diameter circle energy (at 80% energy).

Other design parameters for the lens optimization software include a magnification of at least 10×, and preferably between 10.5× and 11.5×, and a back focal length of 127±2 mm (as seen for surface 15 in the table, a back focal length of 126.731 mm is obtained for the present embodiment), and a wavelength range at least from 400 mm to 700 mm (the entire visible light range). The total length and lens barrel diameter should be as small as possible, i.e. less than 57 mm and 41 mm respectively, since space near the flow cell is in high demand in cytometry instruments. A lens length of 47.2 mm (combined thickness for surfaces 3 to 14) and a maximum aperture radius (for less surfaces 13 to 15) of 17 mm show that these size goals have been met.

The lens is seen to comprise (a) a nearly hemispheric plano-convex crown glass lens (surface 4 through 5 in the above table including the cemented plate of identical material added for handling) with its planar side 4 closest to the cytometry flow cell and its convex surface 5 having a radius of curvature in a range from 3.5 to 5.5 mm (4.66 mm in the present preferred embodiment); (b) a pair of positive meniscus lenses (surfaces 6 to 9) with their concave sides 6 and 8 closest to the flow cell (i.e. on the object side of the lens system) and with the surfaces 8 and 9 of the second meniscus lens being less sharply curved than the corresponding surfaces 6 and 7 of the first meniscus lens, which are in turn less sharply curved than the convex surface 5 of the plano-convex lens; and (c) a pair of positive doublet lens elements (surfaces 10–15) to compensate for chromatic aberrations from the first three lens elements. The near hemispheric shape of the plano-convex lens (total axial thickness of the lens plus the attached plate of identical crown glass material being 4.715 mm compared to the 4.66 mm radius of curvature of the convex surface 5, of difference of less than 1.2%) gives the lens system its large field of view. The convex radius of curvature range provides for a long working distance of at least 1.75 mm (about 2.2 mm in the present embodiment). Use of two meniscus lenses, and also the use of crown glass material (refractive index less then 1.55) for both the meniscus lenses and the plano-convex lens, reduce aberrations, which are generally proportional to the square of the amount of light bending at each refractive surface. The lower aberrations provide improved resolution, as indicated above the image spot size and circle energy. The doublets are not achromats themselves, but are over compensated so that the chromatic aberrations are reduced for the entire lens system.

What is claimed is:

1. A lens system for flow cytometry, comprising:
   a plano-convex lens of a single material of less than 1.55 refractive index with a planar surface thereof defining an object side of the system and with a convex surface having a radius of curvature in a range from 3.5 to 5.5 mm;
   a pair of meniscus lenses having concave surfaces thereof facing the object side of the system, the surfaces of the second meniscus lens being less sharply curved than corresponding surfaces of the first meniscus lens, the convex surface of the first meniscus lens being less sharply curved than the convex surface of the plano-convex lens; and
   a pair of doublet lenses;
   all of the refractive surfaces and distances being optimized for a working distance of at least 1.75 mm, a field of view of at least 400 μm diameter, an RMS spot size in image space of less than 100 μm, and a numerical aperture of at least 1.17 for a lens magnification in excess of 10.

2. The system of claim 1 wherein said plano-convex lens has an axial distance between its planar and convex surfaces which is within 5% of the radius of curvature of its convex surface.

3. The system of claim 1 wherein both of said meniscus lenses are also made of a material of less than 1.55 refractive index.

4. The system of claim 1 wherein said planar surface of the plano-convex lens is optically coupled to a cytometry flow cell via an immersion fluid filling the space therebetween.

5. The system of claim 1 wherein said plano-convex lens includes a plate element and a plano-convex element bonded together, an output surface of the plate opposite the bonded side of the plate element forming the planar optical surface of the plano-convex lens, the plate element forming flanges for ease of handling during assembly of the lens system.

6. A lens system for flow cytometry, comprising lens elements with refractive surfaces defined by:

| Surface | Radius of Curvature | Thickness | Thickness Tolerance | Aperture Radius | Aperture Radius | Material |
|---|---|---|---|---|---|---|
| OBJ | 4 | 0.0889 | — | 0.2 | | Water |
| 1 | 4 | 1.94 | — | 4.6 | | Silica |
| 2 | 4 | 0.1682 | — | 4.6 | | Gel |
| 3 | 4 | 0.8 | .025 | 5.1 | 4.6 | BK7 |
| 4 | 4 | 3.915 | .025 | 4.6 | 4.6 | BK7 |
| 5 (AST) | −4.66 | 1.5 | .025 | 4.6A | 4.6 | Air |
| 6 | −16.918 | 5 | .05 | 8.5 | 7.3 | BK7 |
| 7 | −10.894 | 1 | .025 | 10 | 8.8 | Air |
| 8 | −26.836 | 5 | .10 | 11.5 | 10.2 | BK7 |
| 9 | −15.008 | 1 | .025 | 12.5 | 11.1 | Air |
| 10 | −103.704 | 9 | .10 | 13 | 11.9 | BK7 |
| 11 | −14.012 | 3 | .10 | 13 | 12.2 | SF8 |
| 12 | −34.38 | 2 | .05 | 15.5 | 14.1 | Air |
| 13 | +123.446 | 3 | .10 | 17 | 14.9 | SF8 |
| 14 | +34.38 | 12 | .10 | 17 | 15.1 | BK7 |
| 15 | −36.554 | 126.731 | .50 | 17 | 15.5 | Air |

* * * * *